US008832581B2

(12) United States Patent
Zhang

(10) Patent No.: US 8,832,581 B2
(45) Date of Patent: Sep. 9, 2014

(54) GENE EXPRESSION BROWSER FOR WEB-BASED SEARCH AND VISUALIZATION OF CHARACTERISTICS OF GENE EXPRESSION

(76) Inventor: Ming Zhang, Los Altos, CA (US)

(*) Notice: Subject to any disclaimer, the term of this patent is extended or adjusted under 35 U.S.C. 154(b) by 166 days.

(21) Appl. No.: 12/661,028

(22) Filed: Mar. 5, 2010

(65) Prior Publication Data
US 2010/0235773 A1    Sep. 16, 2010

Related U.S. Application Data

(60) Provisional application No. 61/209,369, filed on Mar. 5, 2009.

(51) Int. Cl.
*G06F 3/03* (2006.01)
*G06F 19/26* (2011.01)
*G06F 19/20* (2011.01)

(52) U.S. Cl.
CPC ................... *G06F 19/26* (2013.01); *G06F 19/20* (2013.01)
USPC ............... 715/771; 705/20; 706/12; 707/769

(58) Field of Classification Search
CPC .................................................. G06F 3/00
USPC ................... 715/771, 721; 702/20
See application file for complete search history.

(56) References Cited

U.S. PATENT DOCUMENTS

| | | | | |
|---|---|---|---|---|
| 5,793,369 A * | 8/1998 | Atkins et al. | ................ | 715/787 |
| 6,263,287 B1 * | 7/2001 | Zheng et al. | ................ | 702/20 |
| 6,301,700 B1 * | 10/2001 | Choi et al. | ................ | 717/116 |
| 6,308,170 B1 * | 10/2001 | Balaban | ................ | 435/6.12 |
| 6,363,399 B1 * | 3/2002 | Maslyn et al. | ................ | 1/1 |
| 6,532,462 B2 * | 3/2003 | Balaban | ................ | 1/1 |
| 6,653,068 B2 * | 11/2003 | Frisch et al. | ................ | 435/5 |
| 7,020,561 B1 * | 3/2006 | McLoughlin et al. | ................ | 702/19 |
| 7,428,554 B1 * | 9/2008 | Coberley et al. | ................ | 1/1 |
| 8,088,971 B2 * | 1/2012 | Song et al. | ................ | 800/278 |
| 8,182,995 B2 * | 5/2012 | Slepnev | ................ | 435/6.12 |
| 8,185,323 B1 * | 5/2012 | Zhuo | ................ | 702/20 |
| 2010/0221725 A1 * | 9/2010 | Slepnev | ................ | 435/6 |

* cited by examiner

*Primary Examiner* — Amy Ng
*Assistant Examiner* — Meseker Takele
(74) *Attorney, Agent, or Firm* — Bo-In Lin

(57) ABSTRACT

Gene Expression Browser is developed for scientists to easily search and visualize the gene expression profiles from large amount of microarray expression data. Web 2.0 technology, full-text searching and server caching are applied to the software application so that large amount data are retrieved very fast from server and are displayed in both clear and comprehensive web user interface. Statistic analysis is hidden from users in the software application. Therefore, the software application is simple to operate and the results are easy to explain. Scientists can easily use the software application without having deep understanding on statistics and data analysis. Gene Expression Browser is the first search and visualization tool for mining large scale and complex microarray data. It might be an alternative to existing complex, slow and expensive microarray data analysis tools.

7 Claims, 18 Drawing Sheets

GENE EXPRESSION BROWSER FOR WEB-BASED SEARCH AND VISUALIZATION OF CHARACTERISTICS OF GENE EXPRESSION

This application claims a priority according to a U.S. patent application 61/209,369 filed on Mar. 5, 2009 by the same Applicant of this Application, the benefit of the filing dates are hereby claimed under Title 35 of the United States Code.

BACKGROUND OF THE INVENTION

1. Field of the Invention

This invention relates generally to microarray technology for displaying and exploring gene expressions. More particularly, this invention is related a gene expression browser by presenting the gene expression profiles into two separate layers, the static and dynamic/responsive presentation layers in order to rapidly view the overall profiles on static data presentation layer, and search/highlight the detail data points in the dynamic responsive presentation layer.

2. Description of the Prior Art

The microarray gene expression data have accumulated in public repositories. The website of NCBI GEO (Gene Expression Omnibus at http://www.ncbi.nlm.nih.gov/geo had collected and annotated 279,089 samples from 10,964 series (experiments) by Jan. 25, 2009. Large amount of raw data and experimental annotations are classified and archived on GEO or EBI servers and are freely available to public. An effective and convenient tool to process and explain the microarray expression data in order to extract meaningful correlations and functional implications to fully utilize and maximize the values of the data becomes a critical issue facing the scientific, research, and medical communities.

Over the past few years, significant efforts have been devoted to develop the micoarray data mining and analysis tools, such as Spotfire, Rosetta Resolver, GeneSpring, TIGR TM4 (Saeed et. al, 2003), Genevestigator (Zimmermann et. al., 2004), Expression Profiler (Kapushesky et. al., 2004), NCBI GEO (Barrett et al., 2005). However, these tools are still difficult to operate due to the complexity in both statistic analysis methods and the large sale of the data. Furthermore, the analysis results are still displayed with heatmaps or x-y plot that is often shown only with limited scopes. Large amount of analysis results are usually shown without dynamically adjustable functional annotations. Therefore, the analytical and mining tools are not intuitive and difficult to comprehend and visualize the correlations between large amount of data even aided with these analysis and display tools. In order to overcome these difficulties, GeneChaser (Chen et. al., 2008) implements a software tool to search and display partial data in text table or bar graphics. The tables and bar graphics show provide simplified data analysis for direct and more intuitive visualization. However, the tool is still limited by the partial search scopes and cannot provide a general overall analysis and display capabilities to enable a dynamic, intuitive and comprehensive visualization of the data correlations among large amount of data now accumulated in the available databases.

As background of this invention, the references listed below provide further references that are relevant to the invention of this Patent Application.

REFERENCES

Barrett, T., Suzek, T. O., Troup, D. B., Wilhite, S. E., Ngau, W., Ledoux, P., Rudnev, D., Lash, A. E., Fujibuchi, W. and Edgar, R. (2005) NCBI GEO: mining millions of expression profiles—database and tools. Nucleic Acids Res. 33, 562-566.

Bolstad, B. M., Irizarry, R. A., Astrand, M., Speed T. P. (2003). A comparison of normalization methods for high density oligonucleotide array data based on variance and bias. Bioinformatics 19, 185-193.

Cao, H., Glazebrook, J., Clark, J. D., Volko, S., and Dong, X. (1997). The *Arabidopsis* NPR1 gene that controls systemic acquired resistance encodes a novel protein containing ankyrin repeats. Cell 88, 57-64.

Chen, R., Mallelwar, R., Thosar, A., Venkatasubrahmanyam, S., and Butte A. J. (2008) GeneChaser: identifying all biological and clinical conditions in which genes of interest are differentially expressed. BMC Bioinformatics 9, 548.

Dudoit, S., Yang, Y. H, Callow, M. J., and Speed, T. P. (2002). Statistical methods for identifying differentially expressed genes in replicated cDNA microarray experiments. Statistica Sinica 12, 111-140.

Irizarry, R. A., Hobbs, B., Collin, F., Beazer-Barclay, Y. D., Antonellis, K. J., Scherf, U., Speed, T. P. (2003) Exploration, normalization, and summaries of high density oligonucleotide array probe level data. Biostatistics 4, 249-264.

Kapushesky, M., Kemmeren, P., Culhane, A. C., Durinck, S., Ihmels, J., Krner, C., Kull, M., Torrente, A., Sarkans, U., Vilo, J., and Brazma, A. (2004). Expression Profiler: next generation—an online platform for analysis of microarray data. Nucleic Acids Res. 32, 465-470.

Kim, J. S., Park, S. J., Kwak, K. J., Kim, Y. O., Kim, J. Y., Song, J., Jang, B., Che-Hun Jung, C. H., and Kang, H. (2006). Cold shock domain proteins and glycine-rich RNA-binding proteins from *Arabidopsis thaliana* can promote the cold adaptation process in *Escherichia coli*. Nucleic Acids Res. 35, 506-516.

Mussgnug, J. H., Wobbe, J. H. L., Elles, I, Claus, C., Hamilton, M., Fink, A., Kahmann, U., Kapazoglou, A., Mullineaux, C. W., Hippler, M., Nickelsen, J., Nixon, P. J., and Kruse, O. (2005). NAB1 Is an RNA Binding Protein Involved in the Light-Regulated Differential Expression of the Light-Harvesting Antenna of *Chlamydomonas reinhardtii*. Plant Cell 17, 3409-3421.

Saeed, A. I., Sharov, V., White, J., Li, J., Liang, W., Bhagabati, N., Braisted, J., Klapa, M., Currier, T., Thiagarajan, M., Sturn, A., Snuffin, M., Rezantsev, A., Popov, D., Ryltsov, A., Kostukovich, E., Borisovsky, I., Liu, Z., Vinsavich, A., Trush, V., Quackenbush, J. (2003) TM4: a free, open-source system for microarray data management and analysis. Biotechniques. 34, 374-378.

Sticher, L., Mauch-Mani, B., and Metraux, J. P. (1997). Systemic acquired resistance. Annu. Rev. Phytopathol. 35, 235-270.

Zimmermann, P., Hirsch-Hoffmann, M., Hennig, L., and Wilhelm Gruissem, W. (2004). GENEVESTIGATOR. *Arabidopsis* Microarray Database and Analysis Toolbox. Plant Physiol. 136, 2621-2632.

In view of these relevant researches and publications, there are three major challenges for mining and viewing the large amount of microarray expression data. The first challenge is the difficulty of displaying complex and large amount of microarray data. A graphic display through a software interface cannot display thousands of data points on a display panel in a clear and comprehensive way to a viewer. Software designers have to make trade-off between two choices. A first choice is to display these thousands of data points completely thus generating images with unprocessed data points that tend to confuse and overwhelm the viewers. Another choice is to display few hundred data points that may appear clear and comprehensive to the viewers but may also miss important data points that are neglected through the selective display processes. The second challenge is the slow computational process caused by the large amount data. Due to the huge volumes of data involved, current computer technology is still confronted with the difficulties to design a software application that has enough computational power to process and in the meantime retrieve such large amount of data in an acceptable speed. This challenge still hinders the practical applications of existing gene expression analysis and display tools even with hardware resources (CPU, memory and network) currently available. The third challenge is the complexities involved in the normalization and analyses of the microarray data. In order to handle the complex tasks of normalization and analysis, current analysis tools are commonly developed as large and complex application software programs. These large and complex software programs thus become inconvenient and complicate to install, maintain and operate and require sophisticate and detail preparations before these programs can be functional for running any gene expression analysis. In order to efficiently analyze microarray expression data, scientists have to have in-depth knowledge of biological theories, statistics, bioinformatics, analysis algorithms and analysis software applications. The existing analytical tools are therefore too cumbersome and inconvenient for practical applications as effective tools to take full advantage of the accumulated data now available for conducting data mining to carry out practically useful gene expression analyses.

Therefore, an urgent need still exists for those involved in the science and technologies of applying the gene express data to develop further simplified and comprehensive tool to explore large amount of microarray expression data.

SUMMARY OF THE PRESENT INVENTION

It is therefore one aspect of this invention is to provide a gene expression browser as a solution for above three challenges such that the above-discussed limitations and difficulties can be overcome.

Particularly, a specific aspect of this invention is to separate the display of gene expression profile into two layers. The first display layer is a static image, e.g., a 60K JPEG file in one exemplary embodiment, to display several thousands of expression data points. The static image of gene expression profile is generated by Java application at server side and can be quickly retrieved into client web browser by users. Therefore, user can quickly obtain gene expression profile by viewing the distribution of data points on the static image. The second layer is dynamic and responsive data annotation layer that is generated by Web 2.0 technology (Javascript/AJAX/Server pages). With the second dynamic and responsive layer, users can get detailed information of the data points on static images by searching and highlighting.

Another aspect of the invention is to improve the performance of data retrieval by applying a server caching technology at the server side. The complex data analyses that involve convoluted statistical concepts and algorithms are now completely hidden from the users by implementing preprocesses that by feeding the data into a high throughput data processing pipeline. Users only type in a key word and then easily obtain complete and comprehensive gene expression profiles. In essence, the Gene Expression Browser of this invention applies a "search and visualization" concept to replace the concepts of "data analysis" used in the conventional microarray data analysis tools. Therefore, the software application is simple to use, the display is clear and comprehensive, the search results are easy to understand and explain. The data retrievals are fast. The data behind the software application are global and complete.

Briefly, in a preferred embodiment, the present invention discloses a gene expression browser wherein the display of gene expression profile is separated into two layers. The first display layer comprises a static image display profile to display several thousands of expression data points. The second layer is dynamic and responsive data annotation layer wherein users can get detailed information of the data points on static images by searching and highlighting In summary this invention further discloses a method to improve the performance of data retrieval by applying a server caching technology at the server side. The complex data analyses with convoluted statistical concepts and algorithms are preprocessed to analyze data with high throughput data processing pipeline. Users can easily obtain complete and comprehensive gene expression profiles by typing in key words. In essence, the Gene Expression Browser of this invention applies a "search and visualization" concept to replace the concepts of "data analysis".

These and other objects and advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

The following descriptions disclose the details of the embodiments of this invention. The descriptions include processes and results of applying the gene expression browser developed according to the two-layer configurations and data analysis and retrieval, correlation and display images implementing the Web 2.0 technologies.

Search in Gene Expression Browser

Users explore gene expression profiles in Gene Expression Browser by searching. Any word in gene annotation, treatment or control description or experiment description can be used for searching. Three types of search result items are returned from the search engine: gene, T/C (treatment over control) and experiment. Click the link on the search result item to visualize Gene View, T/C View or Experiment View respectively.

Gene View

Figure 1:
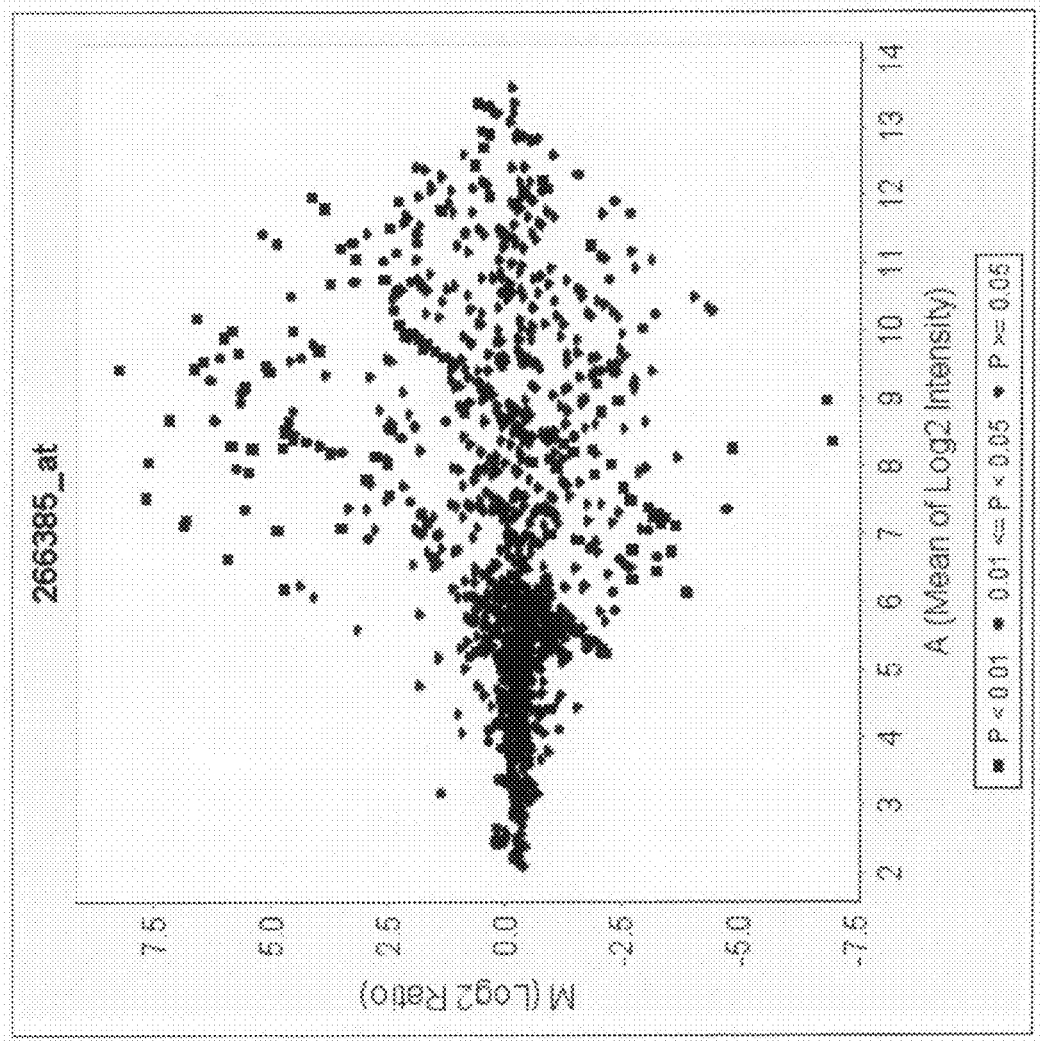
FIG. 1 shows an example of static display layer that shows the gene expression profiles of *Arabidopsis* gene PR-1 (Pathogen Regulated-1). Two benchmarks bands (1.5-fold change and background signal level) are marked on the static image. Each data point is a T/C (Treatment over control). The t-test p values are displayed by color of the data point (blue represents p-value of 0.01 or less; green represents p-value of 0.01-0.05 and yellow represents p-value of 0.05 or more). The image with size of 35 K can be loaded from server to user's client browser very fast. Users can get quick view of gene expression profiles based on the static image.

FIG. 1 shows the Gene View of PR-1 that is an *Arabidopsis* disease-related gene. The up-regulation T/Cs (treatment over control) is selected using the cutoff criteria of 2-fold increase and P value 0.05. Gene View shows all T/C (Treatment over control) experimental conditions on a MA plot (Dudoit et al., 2002; Bolstad et al., 2003). FIG. 1 is an example of the Gene View of *Arabidopsis* PR-1 gene that is a famous disease-related gene (Cao et al., 1997). The data points are draw with blue, green or yellow when t-test P value is lower than 0.01, 0.01-0.05 or higher than 0.05, respectively. The x-axis of MA plot is the log 2 average intensity of treatment and control. The y-axis is the log 2 ratio of treatment over control. Therefore, the data points are up-regulation T/Cs (treatment over control) when they are located at upper location, and are down-regulation T/Cs when they are at bottom location. The treatment and control have higher expression signals when their data points are located at right location, and have lower expression signals when the data points are at left location. Two benchmarks, a horizontal band and a vertical band, are set on MA plot according to 1.5-fold change in y-axis and background signal levels in x-axis. The horizontal band covers all data points within 1.5-fold change. The vertical band on the MA plot covers the background level of 90% experiments. The background is computed for each experiment using the average signals of negative controls in all the chips of the experiment. In current *Arabidopsis* database, there are 142 experiments so that 142 background signals are obtained. The left edge of vertical band is 95th percentile background signal and the right edge of vertical band is 5th percentile background signal.

The MA plot is on a static image with all data points so that users can load the image very fast and quickly get an overall view of the expression profile of a gene. Users can highlight the data points on the image or search the data points by entering key words so that detailed data annotations are projected onto the static image by web 2.0 technology. This two-layer display solution achieves both quick view of overall expression profile and comprehensive view of the detailed information of each T/C that affects the gene expression.

TABLE 1

The T/C* that induces the expression of *Arabidopsis* PR-1 gene.

| T/C* | Treatment Type | P Value*** | Fold Change |
|---|---|---|---|
| BTH Effect for 24 hr in wrky18 mutant | SAR** | 0.0012 | 111.62 |
| senescence effects in pod | others | 2.67E−05 | 97.64 |
| cpr5scv1 double mutant | disease-related mutation | 0.0385 | 88.61 |
| Pst DC3000 infection (12 hr) in WT | infection | 0.0181 | 83.37 |
| BTH Effect for 24 hr in WT | SAR** | 0.012 | 77.47 |
| 120 hr Erysiphe orontii infection | infection | 0.0053 | 64.8 |
| cold 7 days effects | others | 0.0061 | 58.93 |
| cpr5 mutant | disease-related mutation | 0.0354 | 56.63 |
| Pst DC3000 infection (12 hr) in wrky17 mutant | infection | 0.0293 | 55.62 |
| 96 hr Erysiphe orontii infection | infection | 2.50E−05 | 49.32 |
| *Phytophthora* infection for 24 hr | infection | 3.19E−05 | 47.65 |
| 32 hr PsES4326 infection vs 9 hr PsES4326 infection | infection | 0.0267 | 41.11 |
| Pst DC3000 infection (12 hr) in wrky11 mutant | infection | 0.0093 | 37.07 |
| 24 hr PsES4326 infection vs 9 hr PsES4326 infection | infection | 0.0297 | 33.64 |
| E2Fa-DPa overexpressing | others | 0.009 | 32.75 |
| cotyledon | others | 8.69E−05 | 30.2 |
| shoot vs root | others | 8.02E−04 | 29.61 |
| flower stage 15, sepals | others | 1.08E−04 | 28.05 |
| BTH Effect for 8 hr in WT | SAR** | 0.0201 | 26.06 |
| BTH Effect for 8 hr in wrky18 mutant | SAR** | 3.30E−04 | 25.92 |
| cdpk6-yfp 4 transgene effects | others | 0.0151 | 20.98 |
| PsmES4326 infection for 32 hr | infection | 0.0079 | 19.53 |
| PsmES4326 infection for 24 hr | infection | 0.0072 | 16.37 |
| flower stage 15 | others | 1.09E−04 | 14.82 |
| *Pseudomonas syringae* pv phaseolicola infiltration for 24 hr | infection | 0.0015 | 12.87 |
| 72 hr *Erysiphe orontii* infection | infection | 0.0086 | 12.55 |
| old rosette leaf vs young rosettet leaf in WT | others | 0.0235 | 10.82 |
| SPH1 knockout vs WT in young rosette leaf | others | 0.0187 | 10.69 |
| *Pseudomonas syringae* pv tomato avrRpm1 infiltration for 24 hr | infection | 0.0036 | 10.19 |
| flower stage 12 equivalent (7) | others | 3.61E−04 | 8.83 |
| sni1 mutant | disease-related mutation | 0.0117 | 8.59 |

TABLE 1-continued

The T/C* that induces the expression of *Arabidopsis* PR-1 gene.

| T/C* | Treatment Type | P Value*** | Fold Change |
|---|---|---|---|
| flower stage 12 equivalent (6) | others | 2.48E−04 | 8.58 |
| high nitrogen and glucose effects | others | 0.0015 | 7.64 |
| *Pseudomonas syringae* pv tomato DC3000 hrcC-infiltration for 24 hr | infection | 1.75E−04 | 6.78 |
| glucose effects | others | 7.38E−04 | 6.42 |
| flower stage 12, sepals | others | 3.95E−04 | 6.2 |
| arr10 arr12 double null mutant effects under cytokinin | others | 0.0034 | 6.03 |
| cotyledon | others | 3.86E−04 | 5.46 |
| seedling 3 vs average | others | 8.30E−04 | 5.1 |
| seedling 2 vs average | others | 0.001 | 4.87 |
| 16 hr *Pseudomonas* infection | infection | 0.0114 | 4.58 |
| gl1T rosette leaf #4, 1 cm long | others | 1.56E−04 | 4.53 |
| *Pseudomonas syringae* pv phaseolicola infiltration for 6 hr | infection | 0.0308 | 4.33 |
| senescing leaves | others | 3.95E−05 | 4.32 |
| *Botrytis cinerea* infection on 48 hpi leaf | infection | 0.0247 | 4.17 |
| Col-0 rosette leaf #4 | others | 0.0016 | 4.08 |
| WT pathogen treatment 12 hr vs 1 hr | infection | 0.009 | 3.7 |
| gl1T rosette leaf #12 | others | 3.24E−04 | 3.64 |
| flower stage 12 equivalent (5) | others | 0.0028 | 3.62 |
| DC3000hrpA pathogen treatment 12 hr vs 1 hr | infection | 0.0032 | 3.42 |
| leaf | others | 0.0016 | 3.22 |
| cauline leaves | others | 0.0023 | 3.13 |
| shoot under potassium starvation | others | 0.0098 | 3 |
| shoot under Caesium treatment | others | 0.0061 | 2.9 |
| Col-0 rosette leaf #4 | others | 0.0018 | 2.76 |
| 24 hr control vs 0 hr control | others | 0.0158 | 2.7 |
| Ambient CO2 and Ambient Light at 96 hr vs 0 hr | others | 0.0364 | 2.49 |
| rosette leaf # 2 | others | 0.0075 | 2.45 |
| leaf 7, distal half | others | 0.0023 | 2.42 |

*T/C standards for Treatment over Control and represents an experimental condition.
**SAR standards for Systemic Acquired Resistance (reviewed by Sticher et al., 1997).. The SAR is caused by BTH (Benzothiadiazole S-methylester).
***PValue is calculated by the t-test. Two-tailed t-test is used to in to determine the difference between treatment and control. One-tailed t-test is used to determine the difference between treatment and average value of all samples in the experiment.

Figure 2:
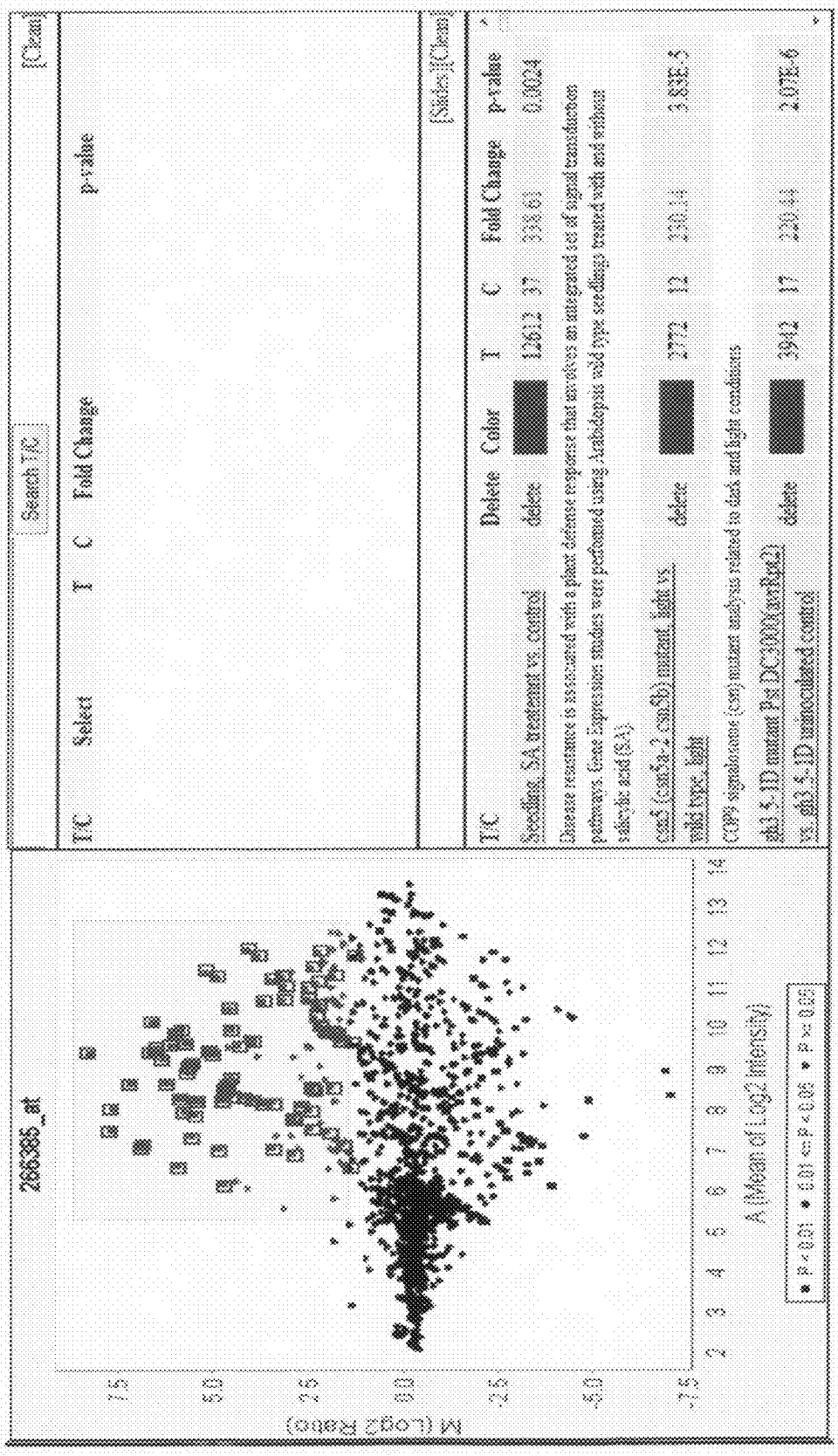
FIG. 2 shows dynamic and responsive data annotation layer on the static image layer. The up-regulation T/Cs (Treatment over Control) of infections, disease-related mutants, SAR (Systemic Acquired Resistance) and others are marked onto static image by highlighting and searching. The up-regulation T/Cs is selected using the cutoff criteria of 2-fold increase and P value 0.05. Therefore, users can get detailed and comprehensive view based on the data annotations.

In FIG. 2, the up-regulation T/Cs are highlighted and displayed on the MA plot. 59 T/Cs increase the expression of PR-1 gene when 2-fold increase and P value 0.05 are used as cutoff (Table 1), in which 17 T/Cs are infection, 4 T/Cs are SAR (Systemic Acquired Resistance) and 4 T/Cs are disease related mutant. It also showed that PR-1 gene over-expresses in the tissues of cotyledon, shoot, leaf and flower (Table 1).

T/C View

Like Gene View, the T/C View is also presented on a MA plot image that shows all genes under a T/C. Each data point on T/C View is a gene. The color of data points and benchmark bands on the plot are defined as same as those in Gene View. Two-layer display is designed for users to highlight and search the genes on the static image as described in Gene View.

FIG. 3 shows the slide views of genes or T/Cs used to discover the changes of multiple genes under multiple T/Cs. Users can make a slide show with multiple Gene Views or with multiple T/C Views. FIG. 3 shows the slide view of 16 cold-related genes. These 16 genes are found by searching keyword "cold" in the gene annotations. The treatment effects of cold, heat, salt, draught and *Pseudomonas* infection are observed on these 16 cold-related genes. FIG. 3A shows that At4g36020 (Affymetrix feature ID 253129_at) in the 16 genes is the gene that is only induced by cold conditions. At4g36020 is reported as cold regulated gene (Kim et. al., 2006) and its homologue in *Chlamydomonas reinhardtii* was reported to be a light-induced gene (Mussgnug et. al., 2005).

Figure 3A:
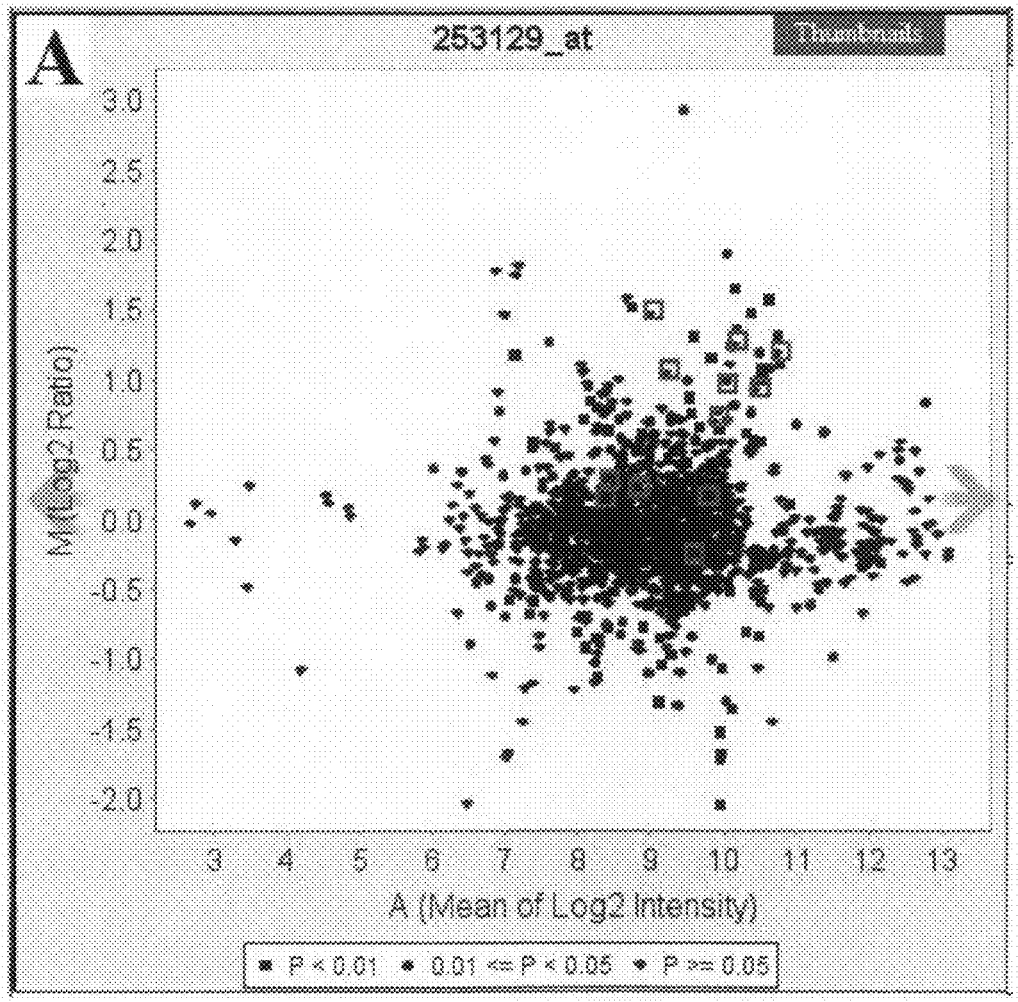
FIGS. 3A to 3P are the slide views of 16 cold-regulated genes (COR genes) that are found by searching keyword "cold" in feature annotation. Each 5 slide include a static image layer that includes all data points and a dynamic and responsive data annotation layer that shows stress-related T/Cs. (A) At4g3602, CSDP1. (B) At2g42540, COR15A. (C) At1g29390. COR314-TM2. (D) At1g29395, COR414-TM1. (E) At1g20440, COR47. (F) At3g05880, RCI2A. (G) At3g05890, RCI2B. (H) At3g50830, COR413-PM2. (I) At5g52310, COR78. (J) At2g15970, COR413-PM1. (K) At1g05260, RCI3. (L) At2g21660, CCR2, GRP7. (M) At4g38680, CSDP2, GRP2. (N) At4g39260, CCR1. (O) At5g15960, AT5G15970, COR6.6, KIN2, KIN1. (P) At2g17870.
Figure 3B:
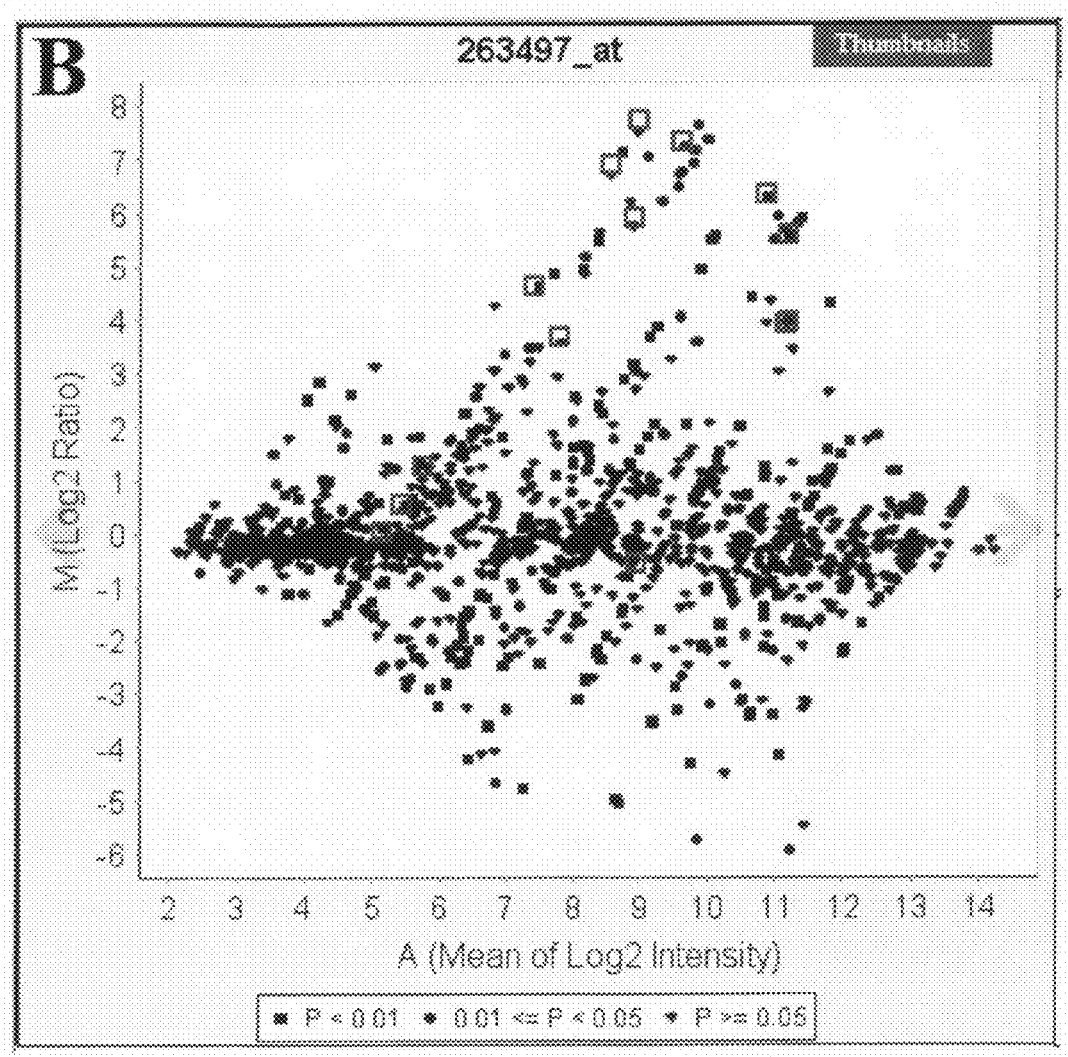
Figure 3C:
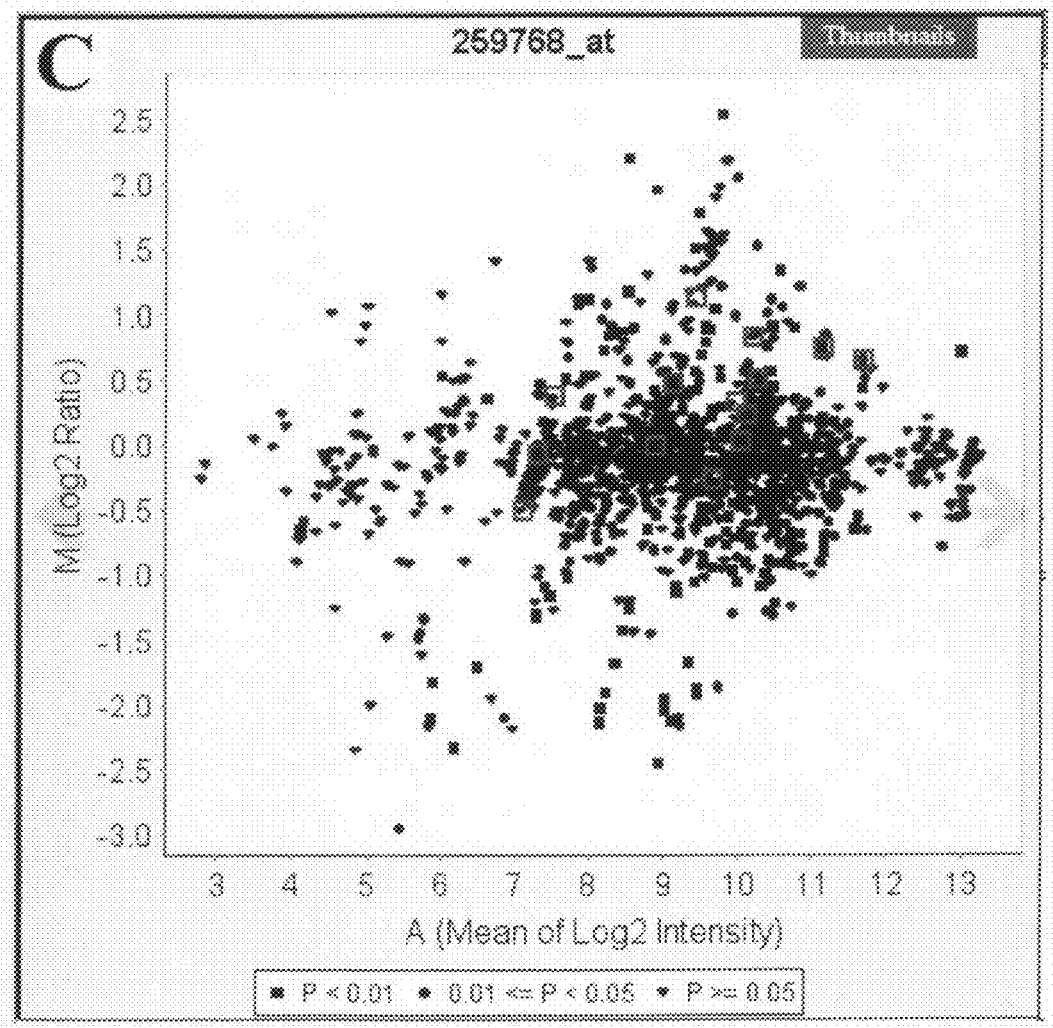
Figure 3D:
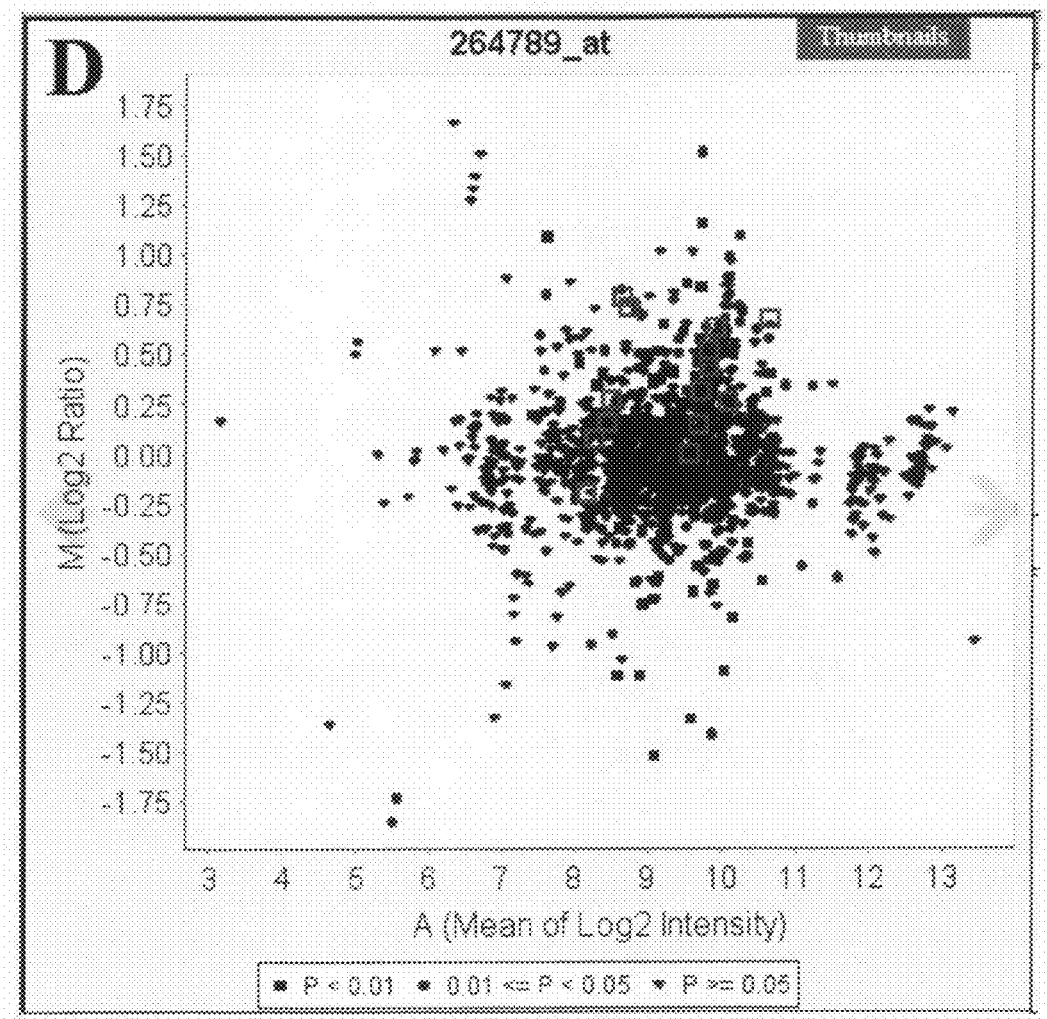
Figure 3E:
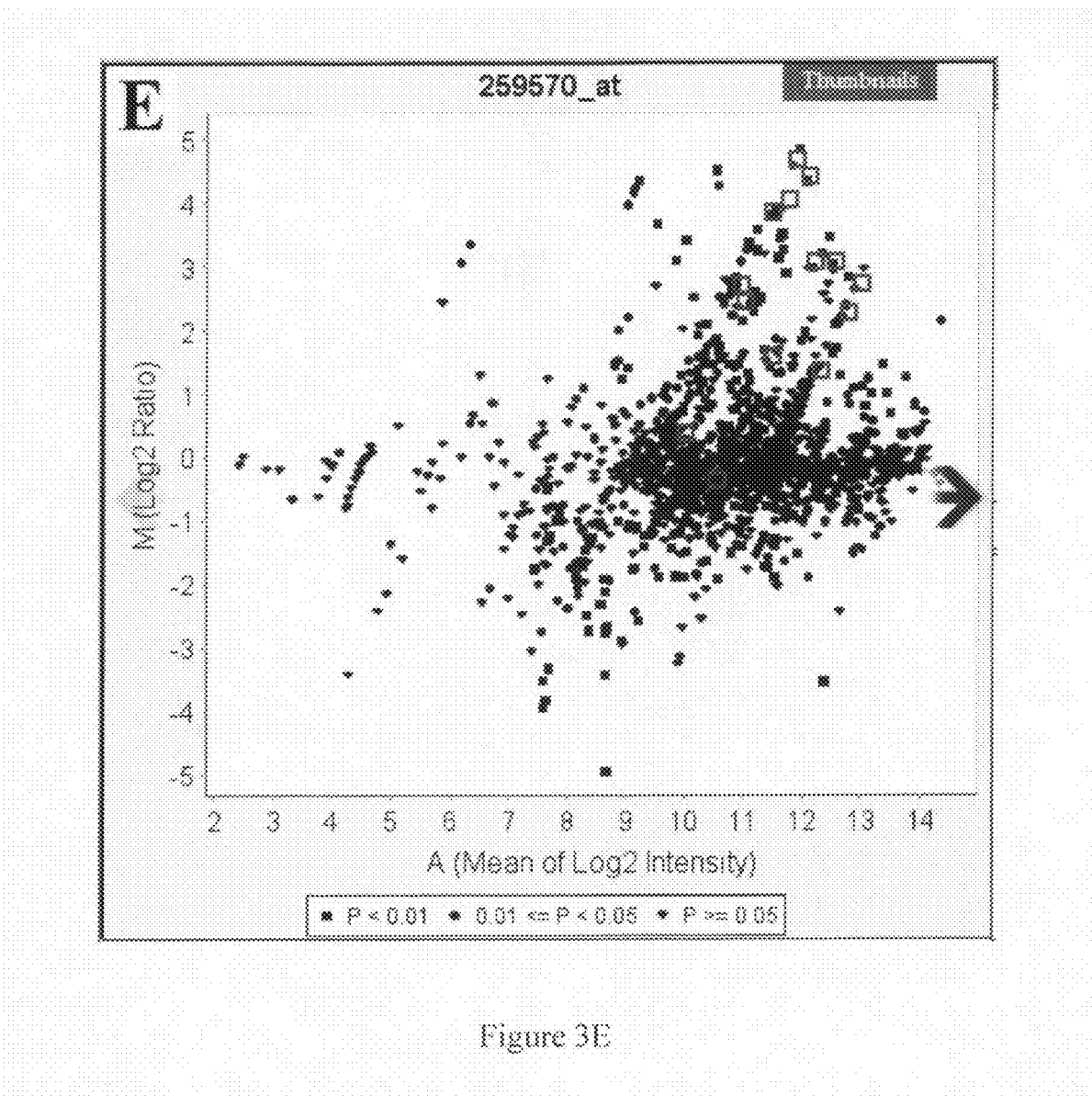
Figure 3F:
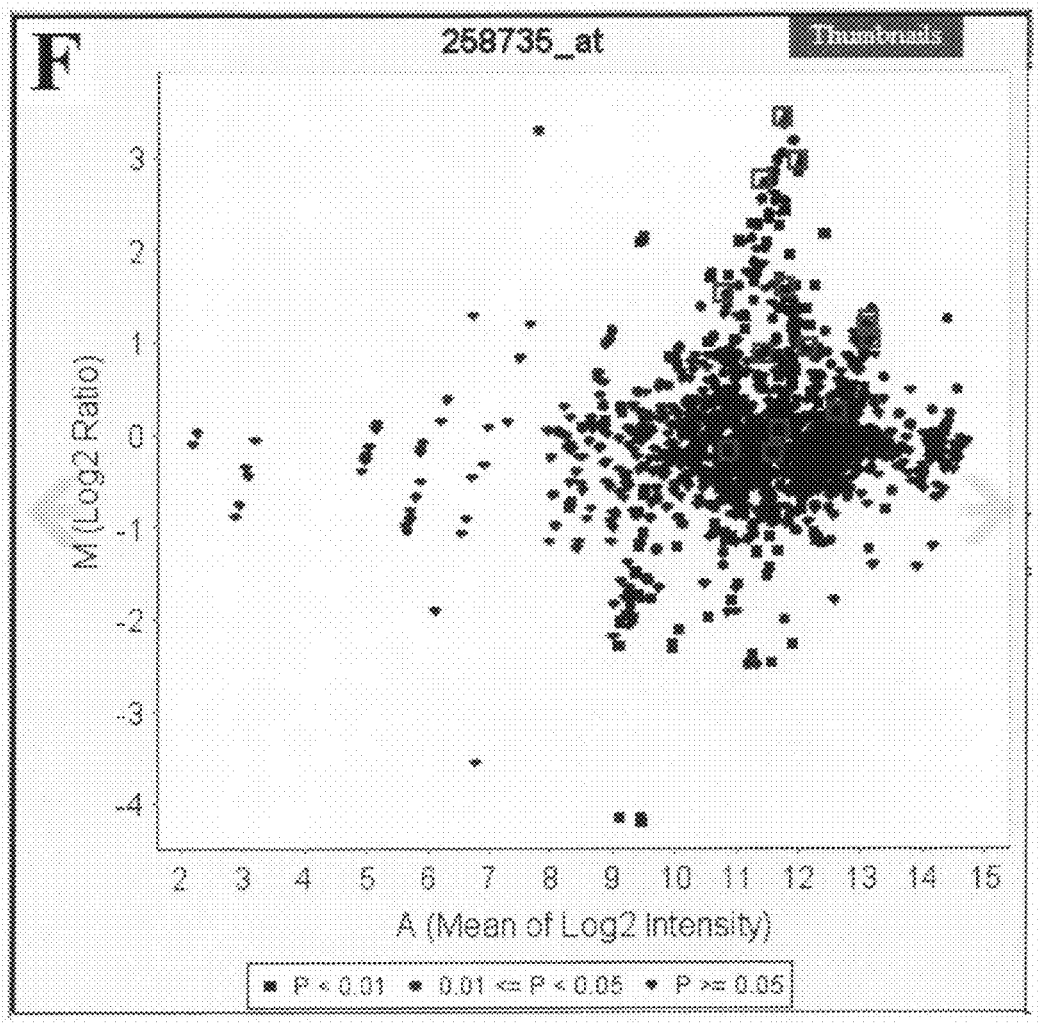
Figure 3G:
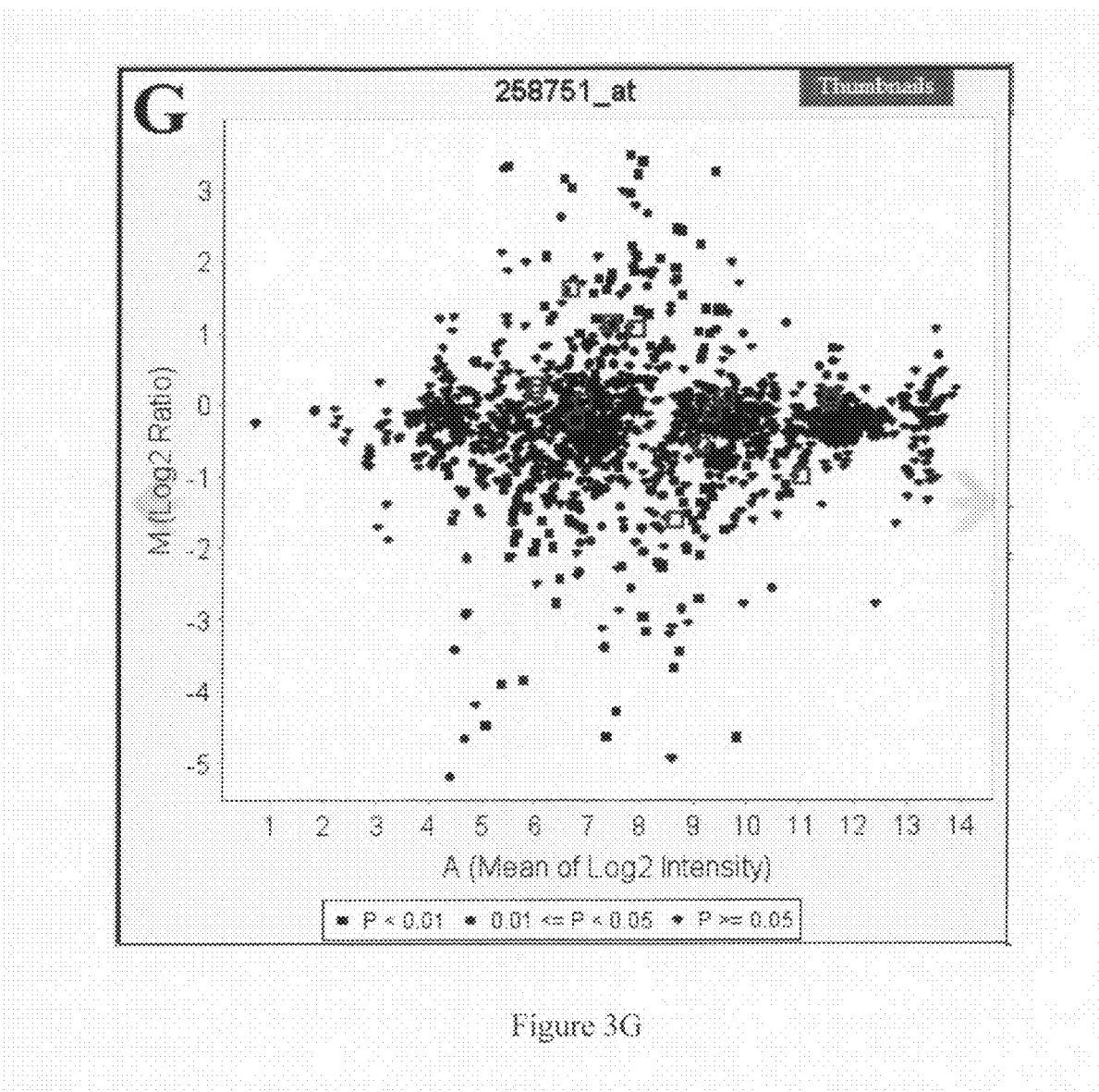
Figure 3H:
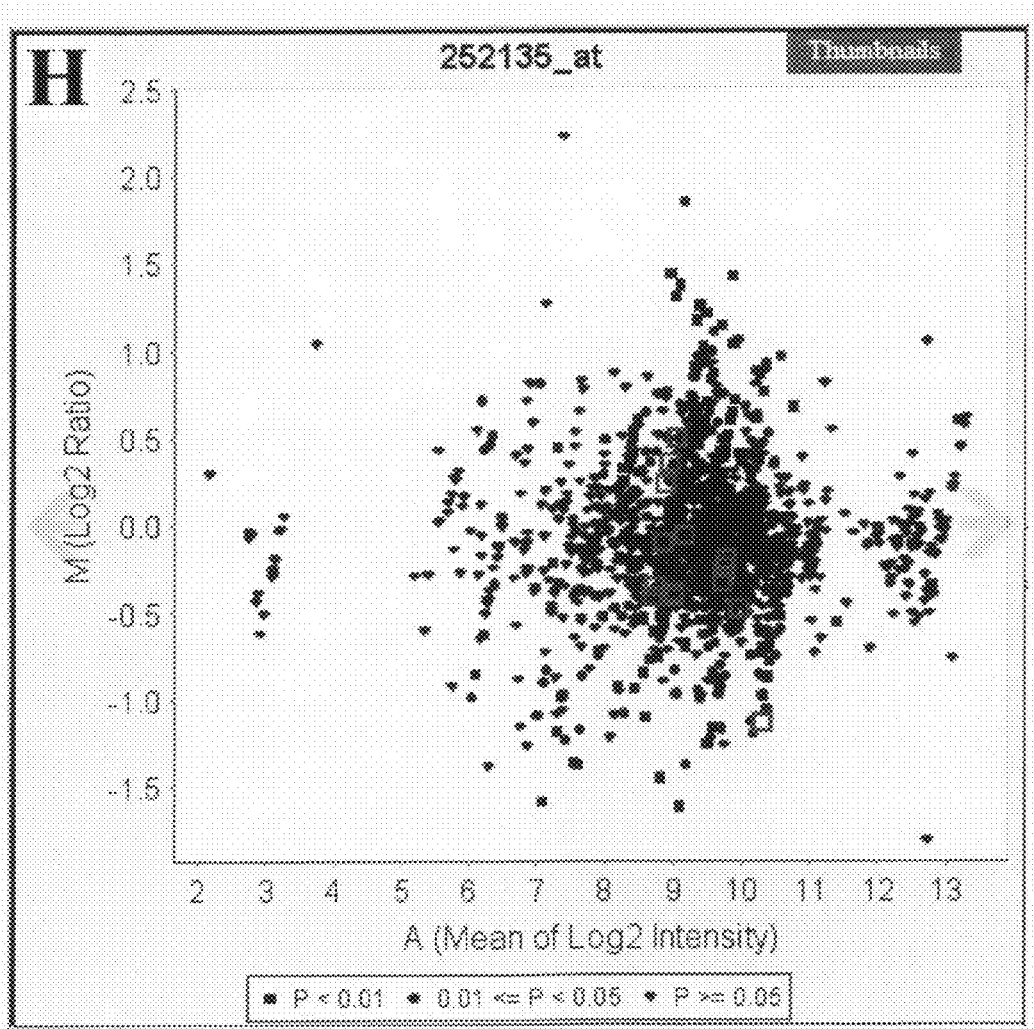
Figure 31:
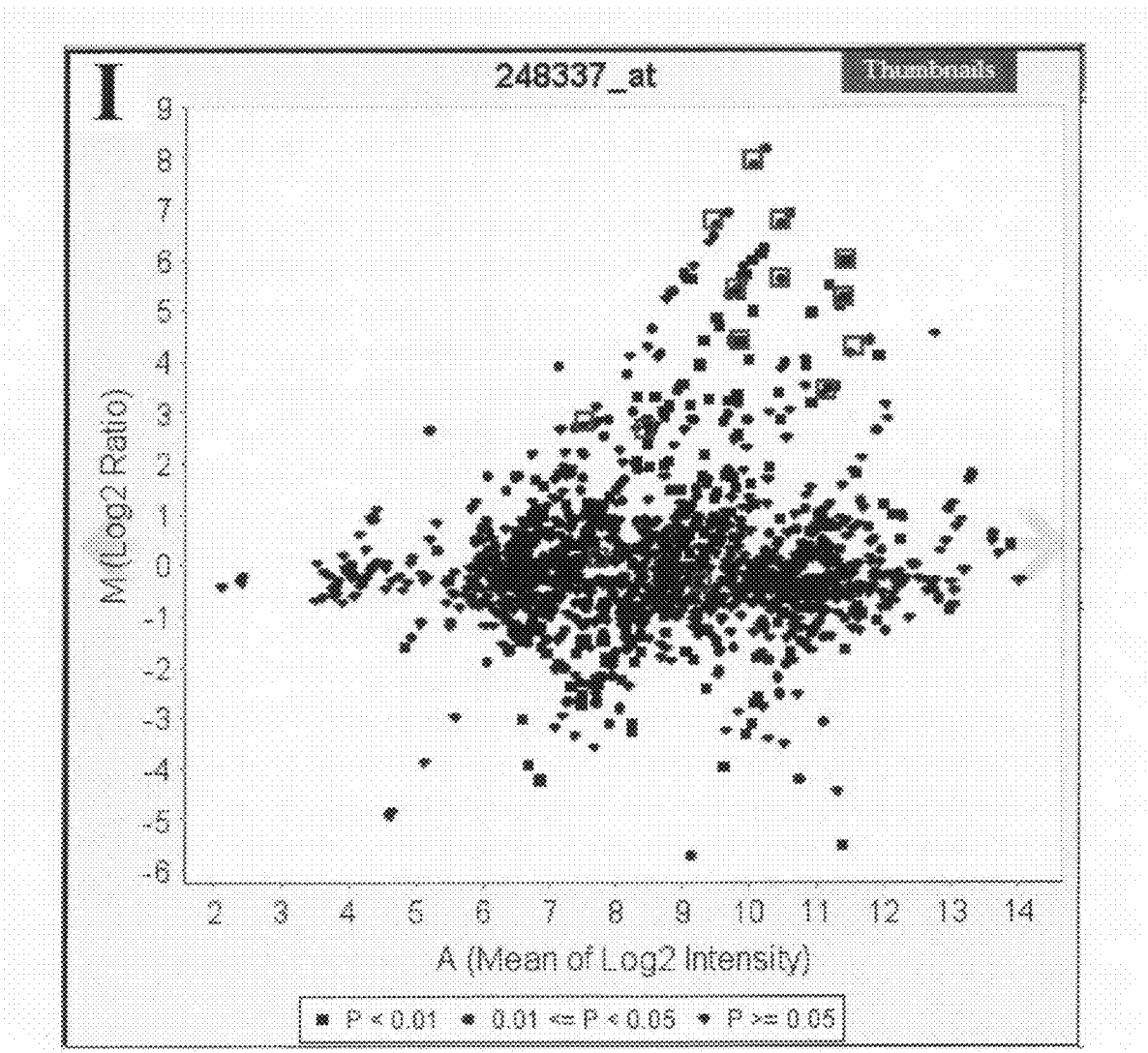
Figure 3J:
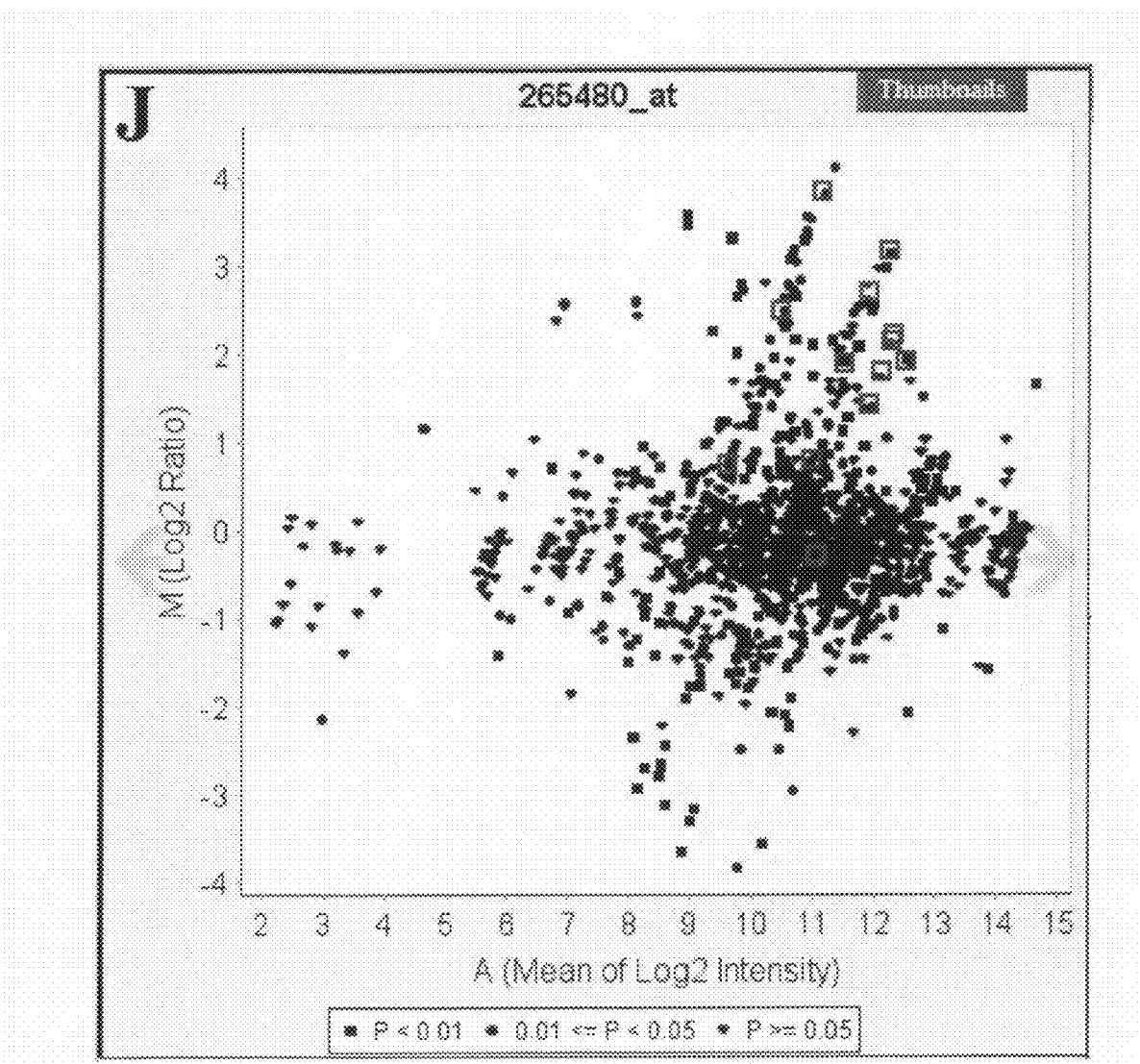
Figure 3K:
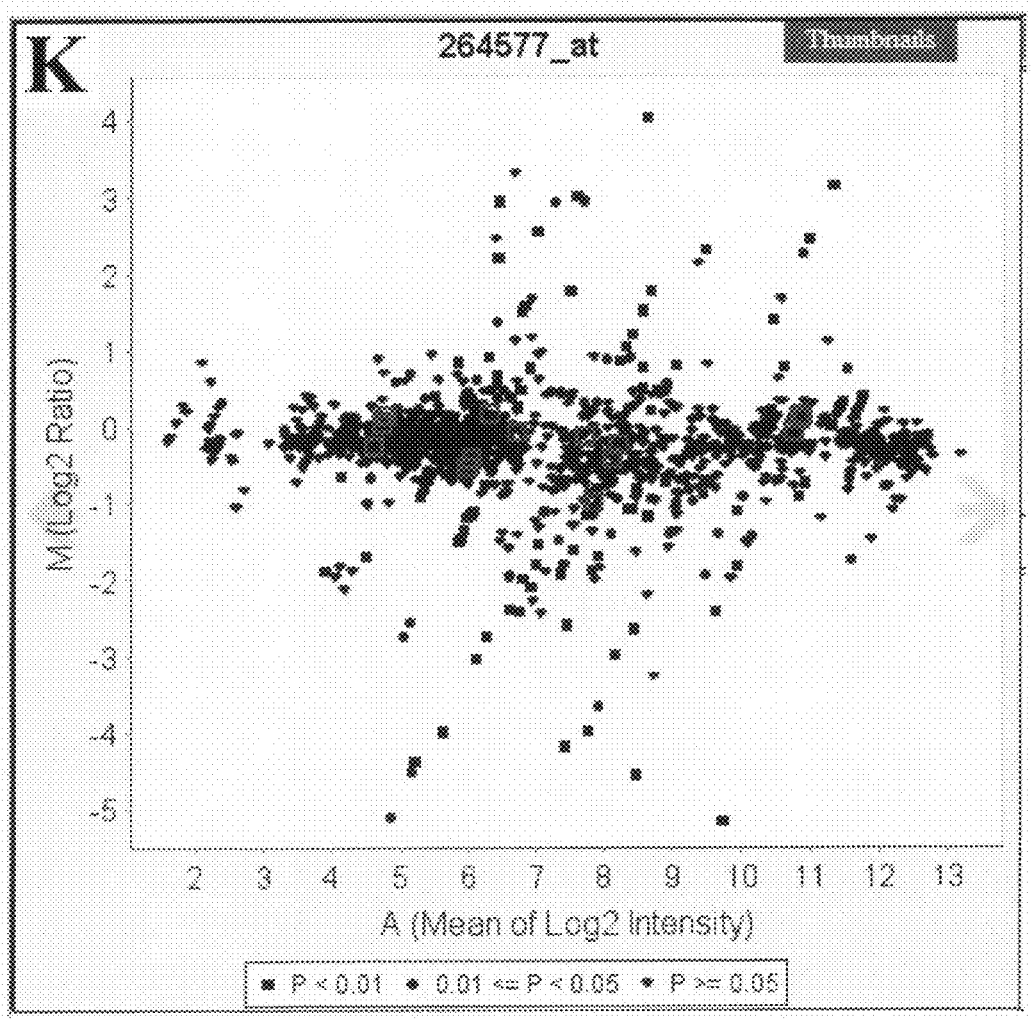
Figure 3L:
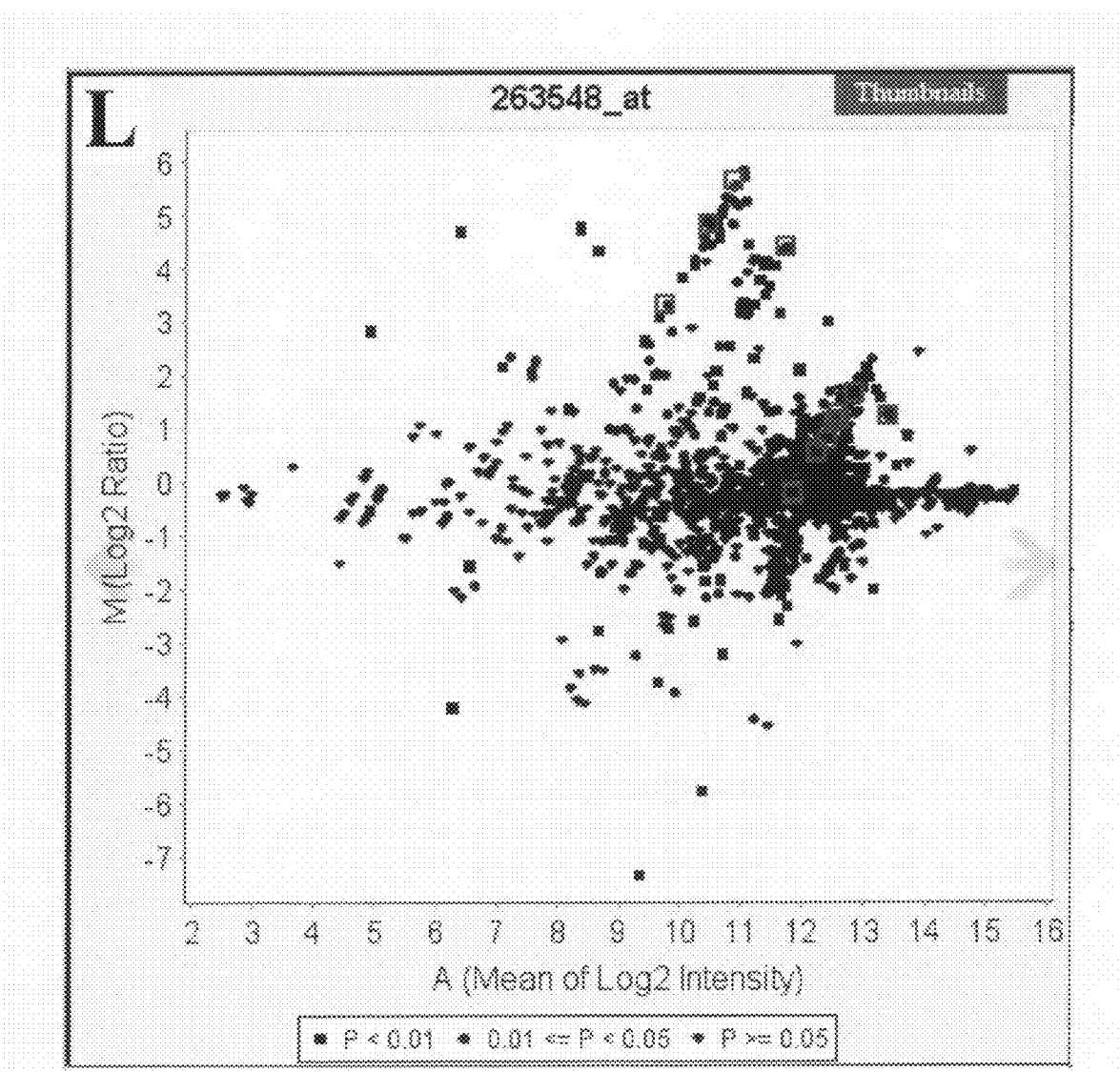
Figure 3M:
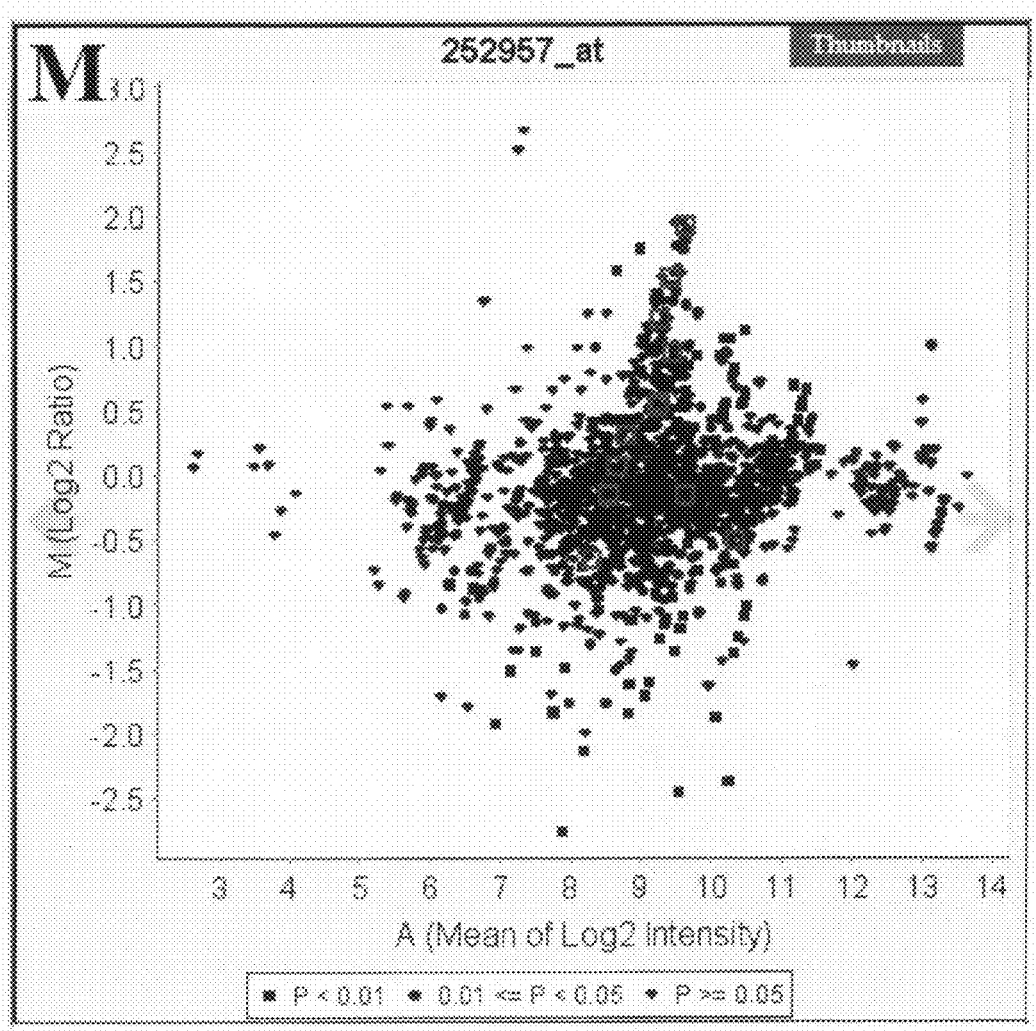
Figure 3N:
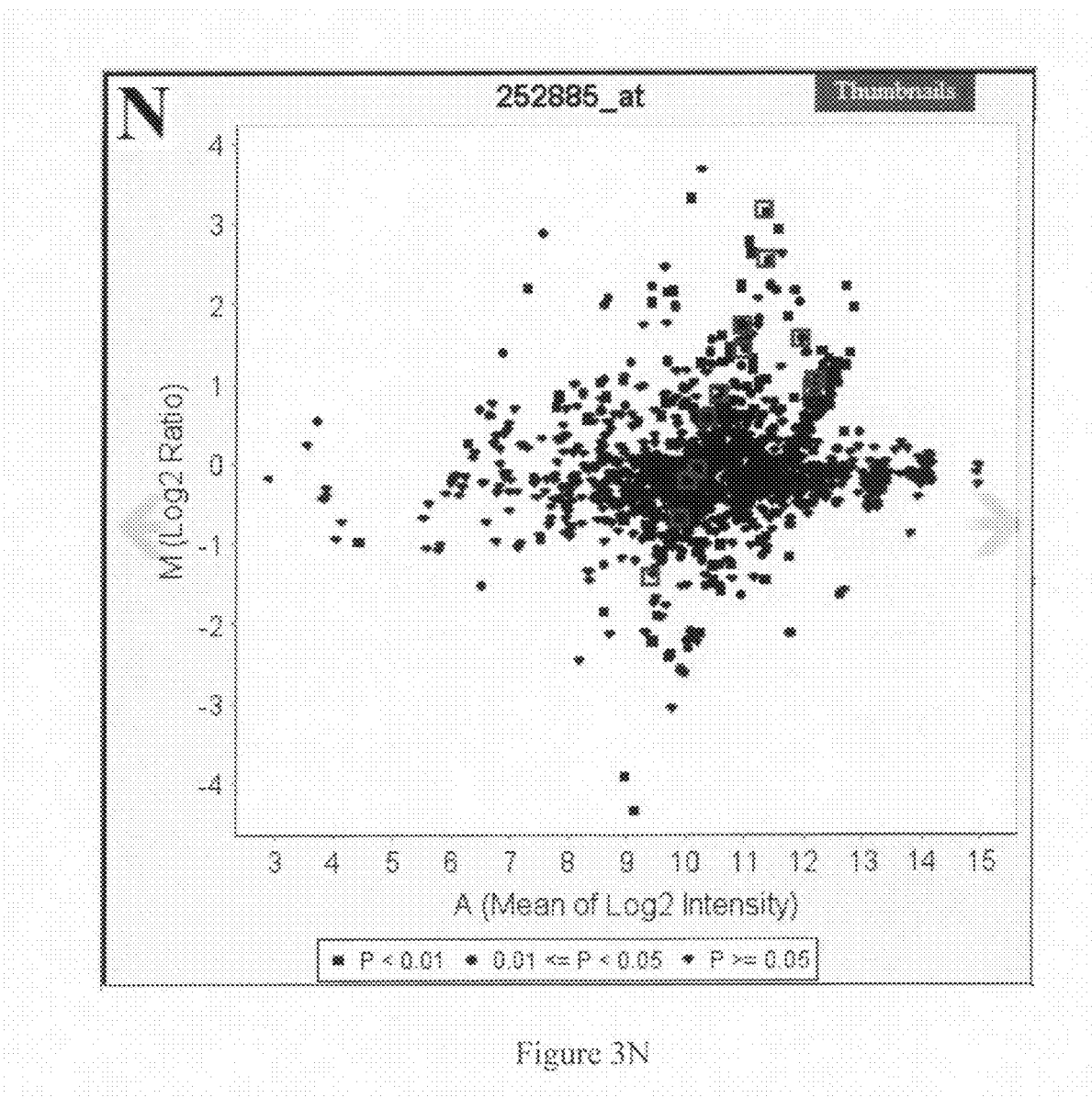
Figure 3O:
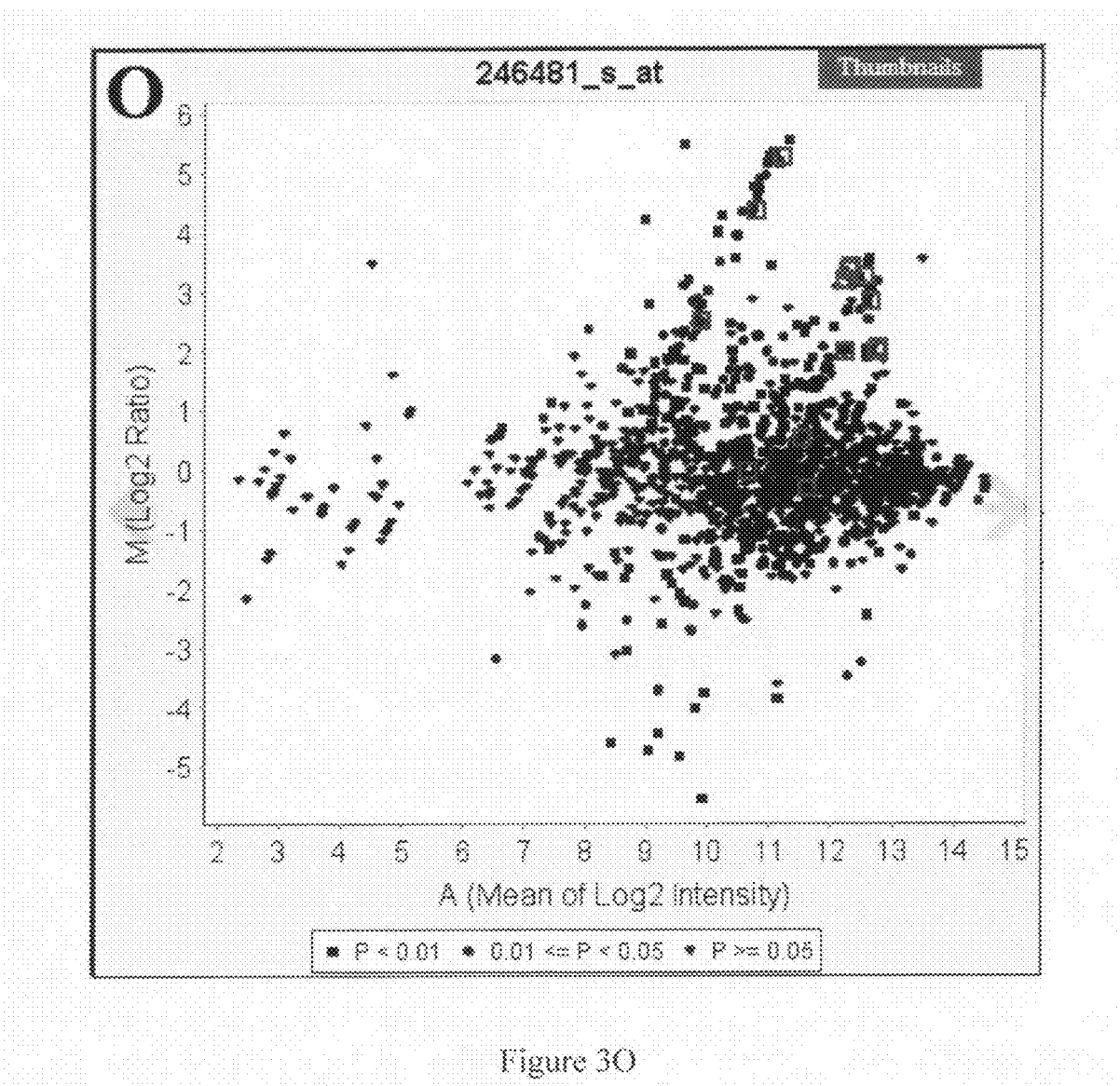
Figure 3P:
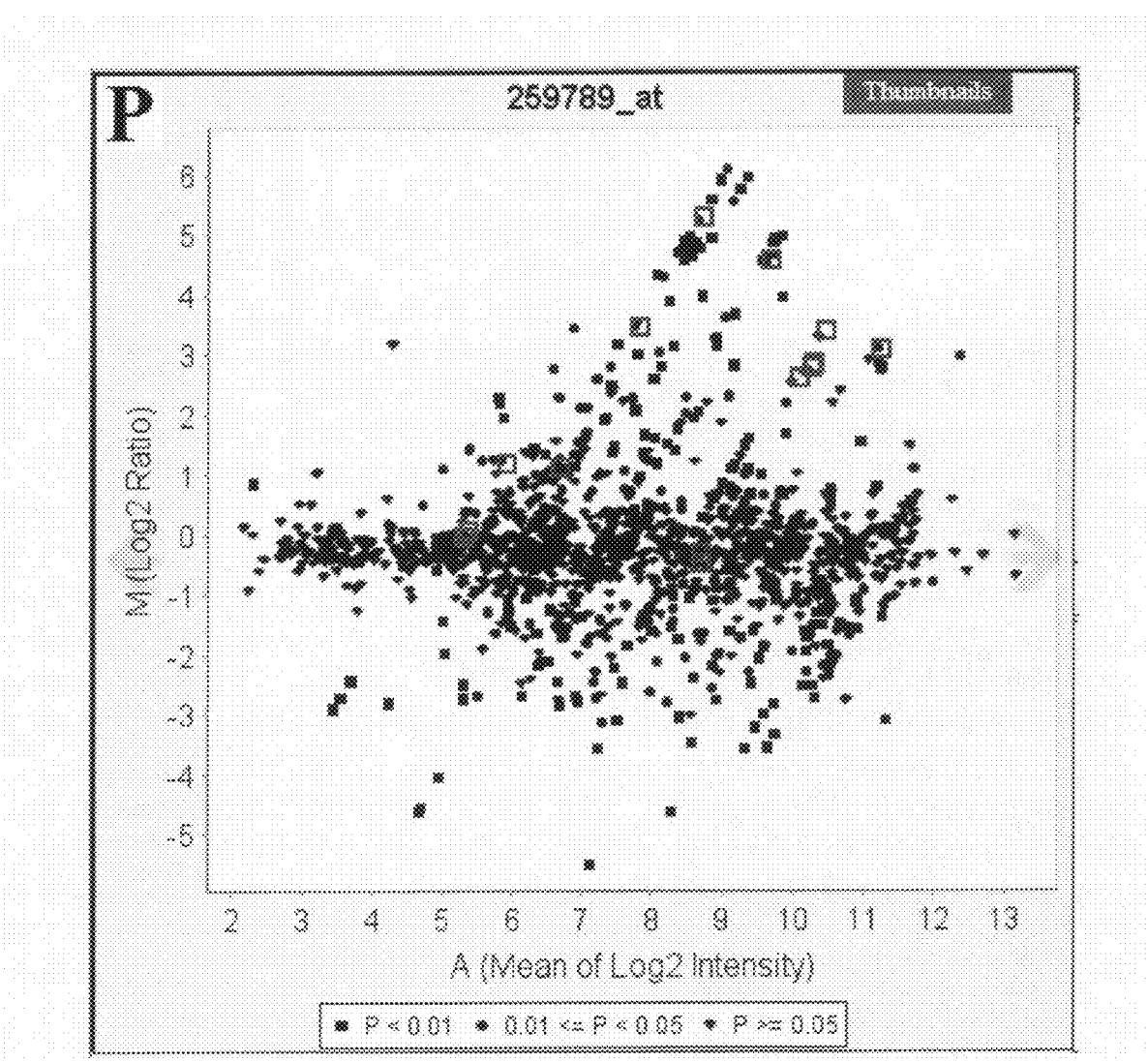

On the other hand, At1g05260 (Affymetrix feature ID 264577_at) is not induced by any stress treatment (FIG. 2K). Other 14 cold-regulated genes are actually stress-induced genes (FIGS. 3B,C,D,E,F,G,H,I,J,L,M,N,O,P). These genes are induced by cold, salt, drought and sometimes by heat. According to FIG. 3, cold stress treatment is closely associated with salt and drought probably because they have similar gene expression regulation mechanism. Heat stress has co-regulation relationship with cold, salt and drought in half cases. On the other hand, *Pseudomonas* infection has completely different regulation trends with cold, salt, drought and heat. It seldom changes the expression of the 16 cold-related genes.

Experiment View

Experiment View is basically a microarray data management system that shows experiment title, description, lab information, samples, biological replicates of each sample, T/C definition and QC scores of the experiment and QC score of each sample in the experiments. The replicate number of a sample is 2, 3 or 4 (The software system rejects all the samples that do not have replicates). The CEL file of each replicate is downloadable from Experiment View. Therefore, users can download the raw data files and input them into other micoarray data analysis software, such as GeneSpring, to validate the results from Gene Expression Browser. Sample QC score is calculated based on the average CV (coefficient of variation) of all microarray genes using the replicates of the sample described in the Experimental Procedures.

The Discovery of Gene Expression Using Gene Expression Browser

Gene expression profiles are easily obtained from Gene Expression Browser by search and visualization. Users can fully under the gene expression profiles by switching among the user interfaces of Gene View, T/C View and Slide View. Users completely get rid of the complex concepts of statistics, data analysis protocols, data input and result explaining. The underneath database includes large amount of expression raw data, normalized data and meta data (average, ratio, P value QC score etc). The web-based interface does not require software download, installation and configuration. Therefore, Gene Expression Browser is a new, simple, convenient, fast, comprehensive, complete and powerful tool for discovering gene expression profiles. The first version of Gene Expression Browser is released together with *Arabidopsis* miroarray data. We will put mouse and human microarray data into Gene Expression Browser to build Gene Expression Browser for Mouse and Gene Expression Browser for Human in near future.

Experimental Procedures

Gene Expression Browser (http://www.Expression-Browser.com) has been built with Java/J2EE/MySQL as the back-end, HTML/Javascript/AJAX (Web 2.0 technology) as front-end, Lucene (http://lucene.apache.org) as full-text search engine and R bioconductor packages (http://www.bioconductor.org) as the core of data processing pipeline. The software application is built on the foundation of open source and freeware libraries, tools and applications (refer to http://www.ExpressionBrowser.com/software.html for details). The first version of Gene Expression Browser is released with 2,435 *Arabidopsis* ATH1 chips (product of Affymetrix Inc) from 142 independent experiments that were collected by NASC's Affymetrix Service (http://affymetrix.arabidopsis.info/AffyWatch.html). The raw data (CEL files) are normalized with RMA (Irizarry et al., 2003) using AFFY package (http://www.bioconductor.org/packages/2.4/bioc/html/affy.html). The pairs of treatment samples and control samples (T/Cs) are defined in each experiment. The average expression intensity of all samples in an experiment is used as control when the control is impossible to define, e.g. the experiments that compare the gene expressions in different tissues. Two-tailed t-test is applied to determine the difference between treatment and control. One-tailed t-test P value is used to determine the difference between treatment and average intensity. The t-test is computed with the Apache Commons Mathematics Library (http://commons.apache.org/math/index.html). The raw data (CEL file), normalized data and meta data (average, standard deviation, ratio, P value, QC score) are stored in MySQL database (http://www.mysql.com) and are retrievable via Gene Expression Browser web application.

The QC score of a sample is calculated by following procedure: (1) Calculate the standard deviation of each gene on microarray based on the sample's replicates. (2) Calculate the CV (Coefficient of Variation=standard deviation/mean) of each gene. (3) Compute the average CV of the sample based on all genes on the microarray. (4) Compute the average CV of each sample in the database according to above procedure 1-3. (5) Generate a normal distribution curve using the CV of all samples. (6) The QC score is calculated by a linear model (QC score=−880*CV+100) that is based on the normal distribution of CV of each sample in the database. QC score ranges from 0 to 100 so that the score is 0 when negative value is obtained from the linear model. The QC score of an experiment is the average QC score of the samples in the experiments.

The gene co-regulation network is built according to the gene expression profiles. The key algorithm for gene co-regulation network is to compute the co-regulation relationship between two genes. The procedure for computing the co-regulation relationship of two target genes is as followings: (1) Find out all T/Cs (treatment over control) that significantly affect the gene expression using certain criteria (1.5-fold change and P value <0.05 are used). As a result, two sets of T/Cs are found from the two target genes. (2) Find out the overlap T/Cs from the two sets of T/Cs. (3) Calculate overlap percentage using formula as overlap ratio=2*overlap T/C number/(T/C number of first gene+T/C number of second gene). (4) Calculate correlation coefficient in the overlap T/Cs using expression log 2 ratios from the two targets genes. (5) Calculate co-regulation index using Overlap ratio*correlation coefficient. (6) Co-regulation index ranges from −1 to 1. Bigger than 0.2 or smaller than −0.2 is suggested to used as cutoff value.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. A data handling and processing device comprising:
   a processor;
   a memory; and
   a gene expression browser executed by the processor comprising:
   a gene expression display separated into two layers wherein a first layer comprises a static image to display several thousands of expression data points as a gene view and for showing the data points of treatment over control (T/C) as a T/C view and also for showing experimental conditions-on the gene view and the T/C view as an experimental view;
   a second layer comprising a dynamic and responsive data annotation layer for on-line real-time web-browser downloading experimental raw data from an experimental raw database for validating the gene expression browser wherein the gene expression browser further includes a user interface to allow users to enter a search term to interactively display detailed data points of the dynamic and responsive data annotation layer based on the experimental raw data downloaded in real-time from the experimental raw database and superimposed on the static images by searching and highlighting the gene expression data and wherein the user interface further allows the users to switch between the gene view, the T/C view and the experimental view; and
   a user interface for receiving a user's real time commands and instructions for displaying and highlighting the complete and comprehensive gene expression profiles on the dynamic and responsive layer according to the user's real time commands and instructions.

2. The data handling and processing device of claim 1 wherein:
   the data handling and processing device is a network device executing a software to carry out functions of the gene expression Web-browser wherein the network device is connected to an Internet.

3. The data handling and processing device of claim 2 wherein:

the gene expression Web-browser further downloading the experimental raw data from the experimental raw database connected via the Internet.

4. The data handling and processing device of claim 3 wherein:

the gene expression Web-browser further downloading the experimental raw data from the d experimental raw database connected via the Internet by applying a Web 2.0 process.

5. A method for carrying out a gene expression display comprising:

applying a high throughput backend data processing pipeline to reprocess and analyze raw data to generate and cache processed data wherein the processed data representing a complete and comprehensive gene expression profiles of each of a plurality of data points for showing a static gene expression image as a gene view and for showing the data points of treatment over control (T/C) as a T/C view and also for showing experimental conditions on the gene view and the T/C view an experimental view;

users entering a keyword to retrieve the complete and comprehensive gene expression profiles to display on the static gene expression image and real-time on-line web-browser downloading experimental raw data from an experimental raw database to show gene expression images as a dynamic and responsive data annotation layer based on the experimental raw data downloaded in real-time from the experimental raw database and superimposed on the static gene expression image by allowing the users to switch between the gene view, the T/C view and the experimental view to complete a search and visualization process; and receiving a user's real time commands and instructions for displaying and highlighting the complete and comprehensive gene expression profiles on the dynamic and responsive layer according to the user's real time commands and instructions.

6. The method of claim 5 wherein:

the step of downloading experimental raw data further comprising a step connecting to the experimental raw database as an Internet database for downloading the experimental raw data.

7. The method of claim 6 wherein:

the step connecting to an Internet database for downloading the experimental raw data further comprising a step of applying a Web 2.0 Web-browser process for downloading and displaying the gene expression images.

\* \* \* \* \*